US012014409B2

(12) United States Patent
Kobayashi et al.

(10) Patent No.: US 12,014,409 B2
(45) Date of Patent: Jun. 18, 2024

(54) HEALTH-RELATED COUNTERMEASURE INFORMATION SYSTEM

(71) Applicant: NICHIYOU HATSUMEI GALLARY Co Ltd., Yaizu Shizuoka (JP)

(72) Inventors: Toyohiro Kobayashi, Yaizu Shizuoka (JP); Akiko Yamada, Yaizu Shizuoka (JP); Tsutomu Miwa, Yaizu Shizuoka (JP)

(73) Assignee: NICHIYOU HATSUMEI GALLARY CO LTD.

( * ) Notice: Subject to any disclaimer, the term of this patent is extended or adjusted under 35 U.S.C. 154(b) by 353 days.

(21) Appl. No.: 17/610,156

(22) PCT Filed: Jul. 17, 2020

(86) PCT No.: PCT/JP2020/027960
§ 371 (c)(1),
(2) Date: Nov. 10, 2021

(87) PCT Pub. No.: WO2021/033474
PCT Pub. Date: Feb. 25, 2021

(65) Prior Publication Data
US 2022/0222725 A1     Jul. 14, 2022

(30) Foreign Application Priority Data

Aug. 22, 2019   (JP) ................................ 2019-151770

(51) Int. Cl.
*G06Q 30/0601*     (2023.01)
*G06K 7/14*          (2006.01)
*G16H 20/00*        (2018.01)

(52) U.S. Cl.
CPC ....... *G06Q 30/0623* (2013.01); *G06K 7/1417* (2013.01); *G06Q 30/0631* (2013.01); *G16H 20/00* (2018.01)

(58) Field of Classification Search
CPC .......... G06Q 30/0623; G06Q 30/0631; G06Q 50/10; G06Q 10/04; G06K 7/1417;
(Continued)

(56) References Cited

U.S. PATENT DOCUMENTS 11,338,107 B2 *   5/2022   Allen ................... H04L 12/2829
2004/0024612 A1*  2/2004   Gerntholtz ............. G16H 50/80
705/2

(Continued)

FOREIGN PATENT DOCUMENTS

JP        2006-71580 A       3/2006
JP        2011-39862 A       2/2011
(Continued)

OTHER PUBLICATIONS

C. Foty, Richard George. "Measuring the Short-Term Effect of Ambient Air Pollution on Acute Health Service use in Ontarians Living with Chronic Obstructive Pulmonary Disease." Order No. 10622502 University of Toronto (Canada), 2017. Ann Arbor (Year: 2017).*

(Continued)

*Primary Examiner* — Amber A Misiaszek
(74) *Attorney, Agent, or Firm* — Yokoi & Co., U.S.A.; Toshiyuki Yokoi

(57) ABSTRACT

To easily know how much a health-related countermeasure product has a countermeasure effect level, and how much countermeasure can be taken against regional weather environment forecast information. A two-dimensional code 1 incorporating countermeasure effect level information for each health-related countermeasure category is attached to a product. On the other hand, there is a mobile terminal device 2 capable of automatically inputting the planned activity amount in exercise and work, the physical condition status, the pulse rate, and the body temperature. The health-related
(Continued)

countermeasures information processing equipment 3 connected to the communication network also obtains weather information such as temperature, humidity and heat index, ultraviolet rays, and pollen scattering amount for each region from the weather forecast prediction data transmission device 4. Then, the necessary countermeasure level is generated. Then, it is determined to be compared with the countermeasure effect level of the product. The result will be useful for selecting the product. In addition, an information system that obtains hindrance occurrence prediction information generated by a deep learning method from the progress history of the above information and related countermeasure product promotion information.

4 Claims, 14 Drawing Sheets

(58) Field of Classification Search
CPC .... G06K 17/0022; G16H 20/00; G16H 10/00; G06F 16/9535
See application file for complete search history.

(56) References Cited

U.S. PATENT DOCUMENTS

| 2007/0004969 | A1* | 1/2007 | Kong | A61B 5/0205 |
| | | | | 128/920 |
| 2013/0024211 | A1* | 1/2013 | Monteforte | G06Q 30/0268 |
| | | | | 705/3 |
| 2013/0217420 | A1 | 8/2013 | Aoike | |
| 2019/0080801 | A1* | 3/2019 | Klos | G16H 40/60 |

FOREIGN PATENT DOCUMENTS

| JP | 2012-114771 A | 6/2012 |
| JP | 2019-28731 A | 2/2019 |
| JP | 2019-86307 A | 6/2019 |

OTHER PUBLICATIONS

International Search Report for PCT/JP2020/27960 dated Sep. 29, 2020.
PCT written opinion dated Sep. 29, 2020.

* cited by examiner

FIG. 3A

Heat Index Forecasts by Region

| Region (City) | | Heat Index (°C) | | | |
|---|---|---|---|---|---|
| | | Today | Tomorrow | The 2 days after | Past Maximum X day, X month, X year |
| Shizuoka | Maximum | 28 °C | 28 °C | 32 °C | 41°C |
| | Average | 27 °C | 26 °C | 30 °C | — |
| | Minimum | 24 °C | 23 °C | 22 °C | — |

FIG. 3B

Required measures level data for heat stroke after correction based on activity amount and physical condition

| Required measures Level and guidelines | Heat index (°C) after correction based on activity status | | | Depends on physical condition and correction value of heat index (°C) | | |
|---|---|---|---|---|---|---|
| | A: Light exercise or work | B: Strong exercise or work | C: Maximum competing exercise or heavy work | 1; It's the same as usual. | 2; A little tired or dullness | 3; Feel heavy body |
| Required measures Level 4; Danger, exercise and work is canceled | 32 °C ~ | 30 °C ~ | 27 °C ~ | 0 | −1 | −4 |
| Required measures Level 3; Strict caution | 29 °C ~ | 27 °C ~ | 24 °C ~ | 0 | −1 | −4 |
| Required measures Level 2; Caution | 25 °C ~ | 23 °C ~ | 21 °C ~ | 0 | −1 | −3 |
| Required measures Level 1; Normal | Less than 25 °C | Less than 23 °C | Less than 21 °C | 0 | −1 | −2 |

FIG. 6A

Ultraviolet Prediction Data by Region

| Region | | Ultraviolet UV Index | | | |
|---|---|---|---|---|---|
| | | Today | Tomorrow | 2 Days after | Past Maximum X day, X, month, X year |
| Shizuoka | Maximum | 10 | 9 | 7 | 13 |
| | Average | 7 | 8 | 5 | 10 |
| | Minimum | 5 | 5 | 2 | 7 |

FIG. 6B

Required Measure level data for Ultraviolet Rays

| Required measures Level and guidelines | Your Skin Situations and UV Index | | |
|---|---|---|---|
| | A: Normal skin | B: Sensitive skin | C: Sunlight-allergic skin |
| Required measures Level 3; Extremely strong vigilance | 11 or more | 10 or more | 8 or more |
| Required measures Level 2; Strong to Very Strong | 6 or more | 5 or more | 5 or more |
| Required measures Level 1; Weak to Medium | 5 or more | 4 or more | 3 or more |

FIG. 9A

Pollen or PM2.5 Scattering Forecasts by Region

| Region | | Pollen or PM2.5 scattering forecast value | | | |
|---|---|---|---|---|---|
| | | Today | Tomorrow | 2 days after | Past Maximum X day, X month, X year |
| Shizuoka Prefecture | Maximum | 40 | 50 | 50 | 70 |
| | Average | 35 | 45 | 45 | 60 |
| | Minimum | 30 | 40 | 40 | 50 |

FIG. 9B

Required measures level data for pollen or PM2.5 countermeasures to be corrected by hypersensitivity

| Required measures Level and guidelines | Correction Required Measures Level for your sensitivity | | |
|---|---|---|---|
| | A: Normal | B: a little sensitive | C: Very sensitive |
| Required Measures Level 3; Very many, vigilance | 50 or more | 40 or more | 30 or more |
| Required Measures Level 2; Many, be careful enough | 30 or more | 20 or more | 10 or more |
| Required Measures Level 1; Slightly large, caution | 10 or more | 5 or more | 5 or more |

FIG. 12A

Two-dimensional code information
for health-related measures products

| Item | Data |
|---|---|
| Classification of health-related measures | Heat stroke measures |
| Level of countermeasure effect | 2 |
| Manufacturer's name or seller's name | coolbit |
| Product Item Number | CBSPCP82-NVY |
| | |

FIG. 12B

Example of communication data from a mobile terminal device to
a health-related countermeasure information processing equipment

| |
|---|
| The Two-Dimensional Code Reading Information |
| Current Location by GPS |
| Mobile device ID No. |
| Regional selection information |
| Selections Date Time Information for Weather Forecast |
| Selection of Activity, Physical condition, , And so on. |

FIG. 12C

Example of communication data from Health-related countermeasure information
    Processing equipment to mobile terminal device (example of heat stroke measures)

| |
|---|
| By Region, Day by Time of Day Health-Related Index Forecast Data |
| Measure level correction data based on the amount of activity |
| Physical condition Other situation Correction data by selection |
| Requirements for vigilance, strict vigilance, etc. Level data |
| Measure Level Pass/NG , Additional Proposals Information |
| New advertising information by purchase history, and more |

FIG. 13A

Example of communication data from Health-related countermeasure information processing equipment to AI processing equipment

| |
|---|
| Health Measures Classification Data |
| Current location or, you can region selection data. |
| Countermeasure effect level data, related Performance details |
| Heat Index data by region |
| Product Manufacturer , Product Item number data |
| Activity amount selection, skin situation selection information and Required measures level correction information |
| Mobile device ID No. |
| User's pulse, body Temperature data |
| User's Physical Condition information |
| Terminal operation information, And so on. |

FIG. 13B

Example of communication data from AI processing equipment to Health-related countermeasure information processing equipment

| |
|---|
| Record highest or maximum data by region |
| Past product purchase history by mobile terminal ID number and appropriately selected health-related measures product information and promotional information |
| Countermeasure correction level data based on past activity amount and skin condition by mobile terminal ID number, Health-related disorder prediction information by ID number by analysis of terminal operation information, And its preventive health related measures proposals and promotional information. |
| |

FIG. 15C

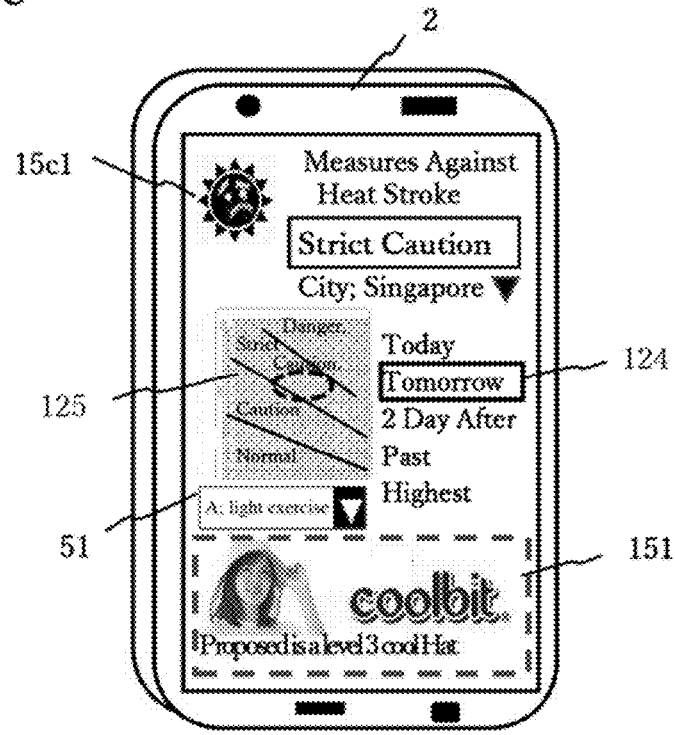

FIG. 15D

```
Tomorrow's heat stroke prediction countermeasure level is "strict     521
caution". Please prepare the XX product of the countermeasure
effective level 3 of the previous purchase. Please take water diligently.
```

```
The product XX you have now is not enough for the heat stroke        522
countermeasure prediction level the day after tomorrow. We
recommend that you prepare for the addition of a new product XXX that
cools your neck.
```

```
From your past product usage history data, heat stroke is "dangerous"  531
according to the predicted activity amount scheduled for tomorrow
entered. We recommend that you review the amount of activity.
```

```
Based on your activity amount, pulse, body temperature measurement
history data and the heat stroke prediction necessary countermeasure   532
level in the XX area the day after tomorrow, the countermeasure product
is XX, and the predicted heat stroke symptom of moderate degree II
"headache" " To prevent "feeling uncomfortable", we recommend taking
Xml / h or more of product XX containing XX ingredients!
```

HEALTH-RELATED COUNTERMEASURE INFORMATION SYSTEM

TECHNICAL FIELD

What is the level of countermeasure (measures) effective for each classification of health-related products?

In addition, how much response and countermeasures can the product be made in comparison with regional weather and environment forecast information such as today and after tomorrow?

Is it an appropriate level of countermeasures for the level of exercise that I plan to do, the amount of activity that accompanies the intensity of work, and the physical condition?

The present invention relates to a health-related countermeasure information system for obtaining related information quickly and easily.

BACKGROUND ART

Patent Document 1 below discloses a portable alarm that can appropriately notify the user of the temperature and humidity conditions according to the place of use.

Furthermore, in recent years, meteorological observation organizations have widely disseminated environmental information by region, such as climate temperature, humidity, ultraviolet intensity, pollen scattering amount, air pollution degree, pressure distribution, and other health-related information through communication lines.

The user receives this with a mobile terminal device, etc., and pays attention to his/her own activities so that it does not simply display, cause a sports accident or a disaster at work.

Alternatively, there is a background that there is already a system in which others monitor.

PRIOR ART DOCUMENTS

Patent Documents

Patent Document 1: JP Patent No; 2019-86307

DISCLOSURE OF THE INVENTION

Problems to be Solved by the Invention

Here, let us consider the sports accident prevention system of Patent Document 1 as a health-related countermeasure system for preventing such sports accidents and accidents during work.

It simply issues cautions and warnings about heat stroke based on the heat index calculated from the GPS detector that knows the current position of the relevant mobile terminal device and the weather environment information such as temperature and humidity for each region. It was a simple functional system.

Recently, many health-related measures such as heatstroke, harmful ultraviolet rays, pollen and other air pollution, and cold weather can be considered as health hazards during sports, outdoor activities, and human activities during work.

Furthermore, at present, the countermeasure products are sold and widely used for each of these health-related countermeasure categories.

However, which of the above health-related measures classification the countermeasure products are, and what level of effectiveness each classification is.

In addition, how much can the product respond to and take measures against the weather conditions in the weather forecast information for each region after today and tomorrow?

Is it an appropriate countermeasure level for the level of exercise that I plan tomorrow and the amount of planned activity that accompanies the intensity of work?

Also, whether it is an appropriate countermeasure level when taking into account your physical condition, etc.

For each health-related measure classification category, the history of past exposure to your own weather index, the amount of exercise and labor activity at that time, and the history of your physical condition, And, is the current countermeasure sufficient compared to the countermeasure level history at that time?

There was a problem that mobile terminal devices could not respond to the demand for quick and easy information on whether there are products with even more effective countermeasures.

Means for Solving the Problem

Therefore, the information system according to the embodiment of the present invention has the following configuration as a means for solving the problem.

For example, a cap-type hat provided with a sunshade that has a cooling function of the back of the head by heat of vaporization is referred to as a "heat stroke countermeasure product" as a product according to health-related countermeasure categories.

Then, attach two-dimensional code information such as a QR code (registered trademark) that incorporates the information to the hat.

In addition, hat-type hats that have a harmful ultraviolet ray shielding effect are also accompanied by two-dimensional code information that incorporates information called "harmful ultraviolet rays countermeasure" as a product for each health-related measure classifications.

Similarly, similar two-dimensional code information can be attached to products by various health-related countermeasure classifications such as "pollen countermeasure and PM2.5 air pollution countermeasure".

A mobile terminal device connected to a communication network such as the Internet that reads this two-dimensional code information is provided.

On the other hand, it receives information from the weather forecasting agency that transmits weather data information such as temperature, humidity, harmful ultraviolet rays, pollen and PM2.5 air pollution scattering amount, etc. by region to the communication network, and required countermeasure for each health-related measure classification category.

A health-related measure information processing equipment that selects and generates information and transmits the information to the communication network is provided so that the portable terminal device can display the transmitted information.

Further, the means of the system of one embodiment has the following configuration.

As the information to be incorporated into the two-dimensional code, the countermeasure effective level is incorporated for each health-related countermeasure classification.

For example, a cap-type hat provided with a sunshade having a cooling function is set to "heat stroke countermeasure effect level 1".

And a cooling vest, which is said to have a greater countermeasure effect, it is set to "heat stroke countermeasure effect Level 2" of the two-dimensional code is attached.

On the other hand, a health-related information processing equipment is provided to receive the meteorological data information from the meteorological forecast data transmitting equipment of the meteorological forecasting organization according to the predicted date and time such as region, tomorrow, and the day after tomorrow.

The information processing equipment processes the weather data information into a heat index, UV index value, pollen scattering distribution map, for each region, and generate countermeasure information, normal, caution, strict caution, dangerous work cancellation, etc., such like the required countermeasures level information.

Here, the countermeasure effect level of the two-dimensional code information attached to the product is compared with the required countermeasure level, and the result can be displayed on the mobile terminal device.

It is designed to help determine whether the countermeasure is effective or appropriate.

Further, the means of the system of other one embodiment has the following configuration.

The mobile terminal device is provided with a means for inputting or detecting the current or planned amount of activity in exercise or work, or the physical condition such as pulse, body temperature, skin condition, and hypersensitivity condition.

The health-related measure information processing device is configured so that the required measure information and the required measure level information can be corrected and changed based on the information input by the means and displayed on the mobile terminal device.

Further, the means of the system of other one embodiment has the following configuration.

By mobile terminal device specified by mobile phone number or ID number entered by the user, by the above-mentioned health countermeasure classification, required countermeasure level information, activity amount, physical condition information, and required countermeasure report after correction for the user-specified has a means of accumulating.

The mobile terminal also provides means for comparing, organizing and accumulating these in chronological order, and for each of the above categories, related classification-specific hindrance occurrence prediction information, countermeasure recommendation enlightenment information, and related product promotion information generated by the AI processing device. They are configured to be displayed on the device.

Further, here, instead of the two-dimensional code, the information obtained by linking from the mark for each health measure classification or the product image on the WEB is converted into the same information as that incorporated in the two-dimensional code. Add that even if they are replaced, it will be the same solution.

Effects of the Invention

The effects of the first embodiment of the present invention are as follows.

With a mobile terminal device, only by reading the two-dimensional code attached to the product for each health-related measure classification, or by simply linking from the mark indicating the health-related measure classification on the WEB, temperature, humidity, amount of ultraviolet rays, It is very useful for health-related counter-measure because it is possible to promptly and appropriately obtain each required measure information and required countermeasure level information calculated based on regional meteorological data such as the amount of pollen scattered.

In addition, not only by health-related measure classification, but also by incorporating the measure effect level information of that classification into the product, it is configured so that it can be compared with the required measure level in the future such as tomorrow and the day after tomorrow. It is effective in preparing for health-related countermeasure and as a guide for purchasing products.

The effects of the second embodiment of the present invention are as follows.

Enter the amount of activity for current or planned heat stroke countermeasures during exercise or work, or the physical condition such as pulse, body temperature, skin condition for harmful ultraviolet rays countermeasures, and hypersensitivity status for pollens or PM2.5 countermeasures. Since the means is provided in the mobile terminal device, it is configured to correct the required countermeasure level according to the amount, situation, and degree of the means, so that more detailed countermeasure can be taken according to the individual situation of the user. These have very useful effects.

The effects of the third embodiment of the present invention are as follows.

Accumulates health measure classification, required measure level information, activity amount, physical condition information, and required measure information after correction by individual specified by mobile phone number or ID number entered by the user.

There is a way to do it. In addition, a means for comparing and organizing these in chronological order is provided.

Therefore, it is effective to be able to quickly see the hindrance occurrence prediction information for each related classification, the countermeasure recommendation enlightenment information, and the related product promotion information generated by the AI processing device on the mobile terminal device.

Since the present invention is such a thing, it has a feature that it can be applied to various kinds of health-related products.

It has a great effect and is very significant industrially as it can be applied not only to heat stroke countermeasure products, but also to harmful ultraviolet rays countermeasure products, air pollution countermeasure products such as pollinosis or PM2.5, and cold protection countermeasure products.

BRIEF DESCRIPTION OF THE DRAWINGS

FIGS. 3A and 3B are charts related to the data used in this embodiment, and FIG. 3A is by region and an example of heat index prediction data, FIG. 3B shows the amount of activity and heat after correction based on physical condition. This is an example of required countermeasure level data for illness.

FIGS. 6A and 6B are charts relating to the data used in the embodiment of the present invention, and FIG. 6A is an example of ultraviolet prediction data for each region. FIG. 6B shows the level of necessary countermeasures for harmful ultraviolet rays based on the corrected UV index, taking into account the skin condition as the physical condition. This is an example of data.

FIG. 9A is an example of pollen scattering prediction data by region and time. FIG. 9B is an example of the required countermeasure level data for pollen countermeasures to be corrected by the degree of hypersensitivity.

FIGS. 12A to 12C are charts relating to data used in the embodiment of the present invention. FIG. 12A is an example of 2D code information for health-related products. FIG. 12B is an example of communication data from a mobile terminal to a health-related information processing device. FIG. 12C is an example of communication data (an example of heat stroke countermeasures) from a health-related countermeasure information processing device to a mobile terminal.

FIGS. 13A and 13B are charts regarding the data used in the embodiment of the present invention. FIG. 13A is an example of communication data from the health-related measure information processing device to the AI processing device, and FIG. 13B is an example of communication data from the AI processing device to the health-related measure information processing device.

FIGS. 15A to 15D are display examples of the mobile terminal device of the present embodiment is shown, and FIG. 15A shows a display example of "harmful ultraviolet rays countermeasures" as a health-related countermeasure classification. FIG. 15B shows an example of display in "Pollen and PM2.5 Countermeasures". FIG. 15C is a diagram showing a display example in the same "heat stroke countermeasure". Further, FIG. 15D is shown on the display unit of the mobile terminal device generated by the AI processing equipment. It is a figure which shows the display example of required countermeasures information, enlightenment information, and promotion information.

MODES FOR CARRYING OUT THE INVENTION

Hereinafter, embodiments and examples of the present invention will be described with reference to the drawings below.

Figure 1:
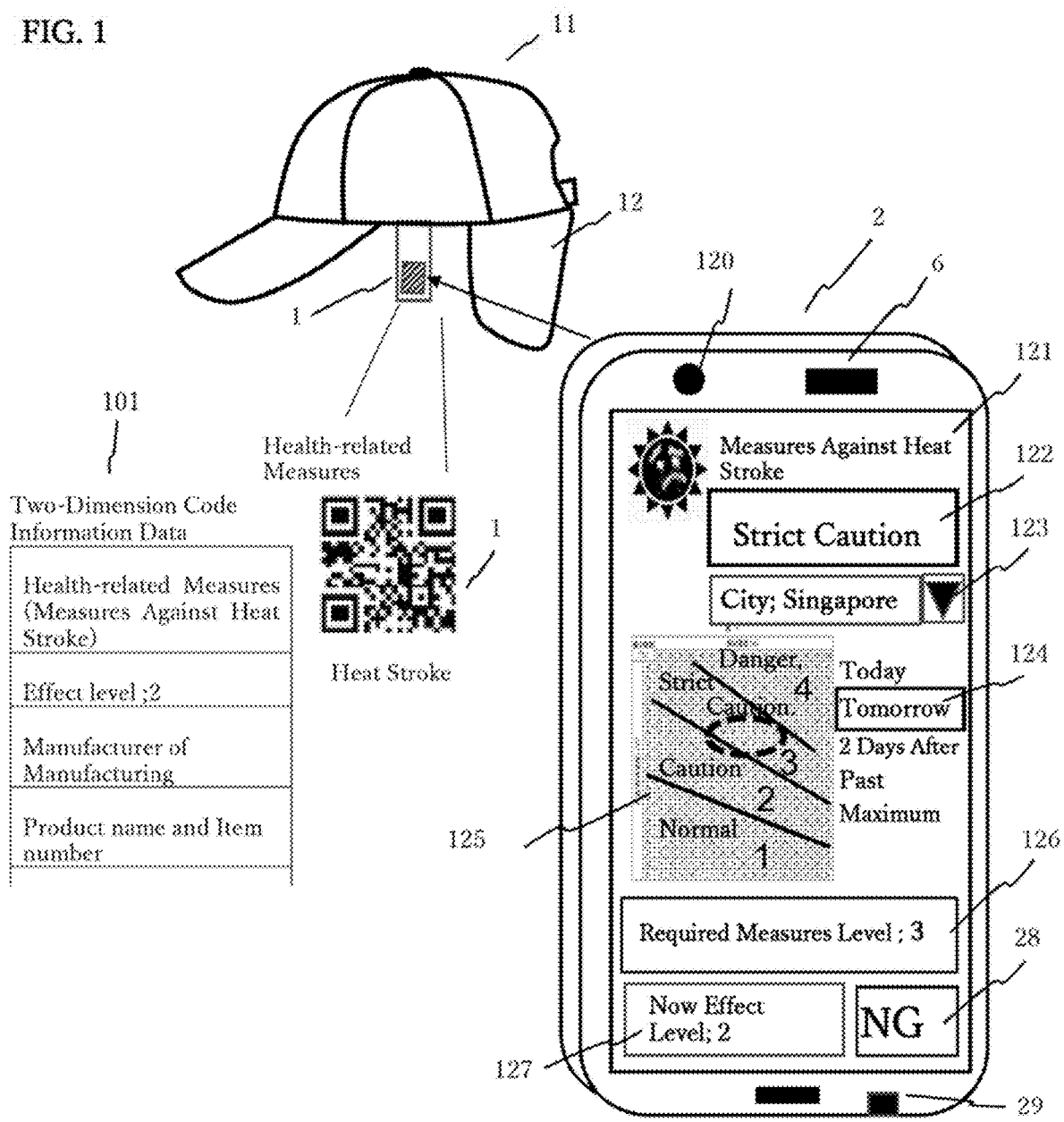
FIG. 1 is an explanatory diagram showing a usage state of a system according to an embodiment of the present invention.
Figure 2:
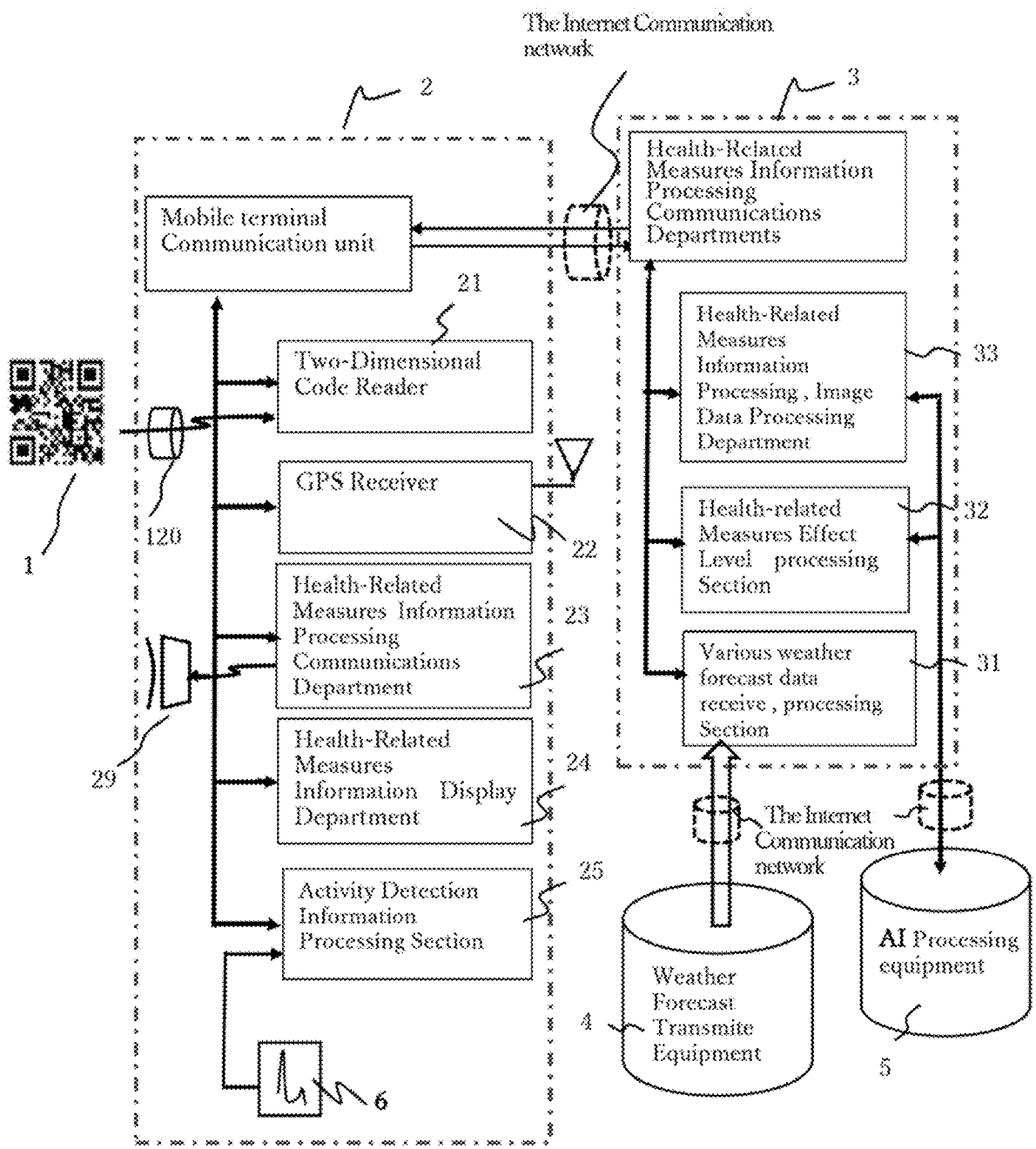
FIG. 2 is a configuration diagram of the system in this embodiment.

FIG. 1 is an explanatory diagram showing a usage state of a system according to an embodiment of the present invention. FIG. 2 is a configuration diagram of the system according to the present embodiment.

Figure 14:
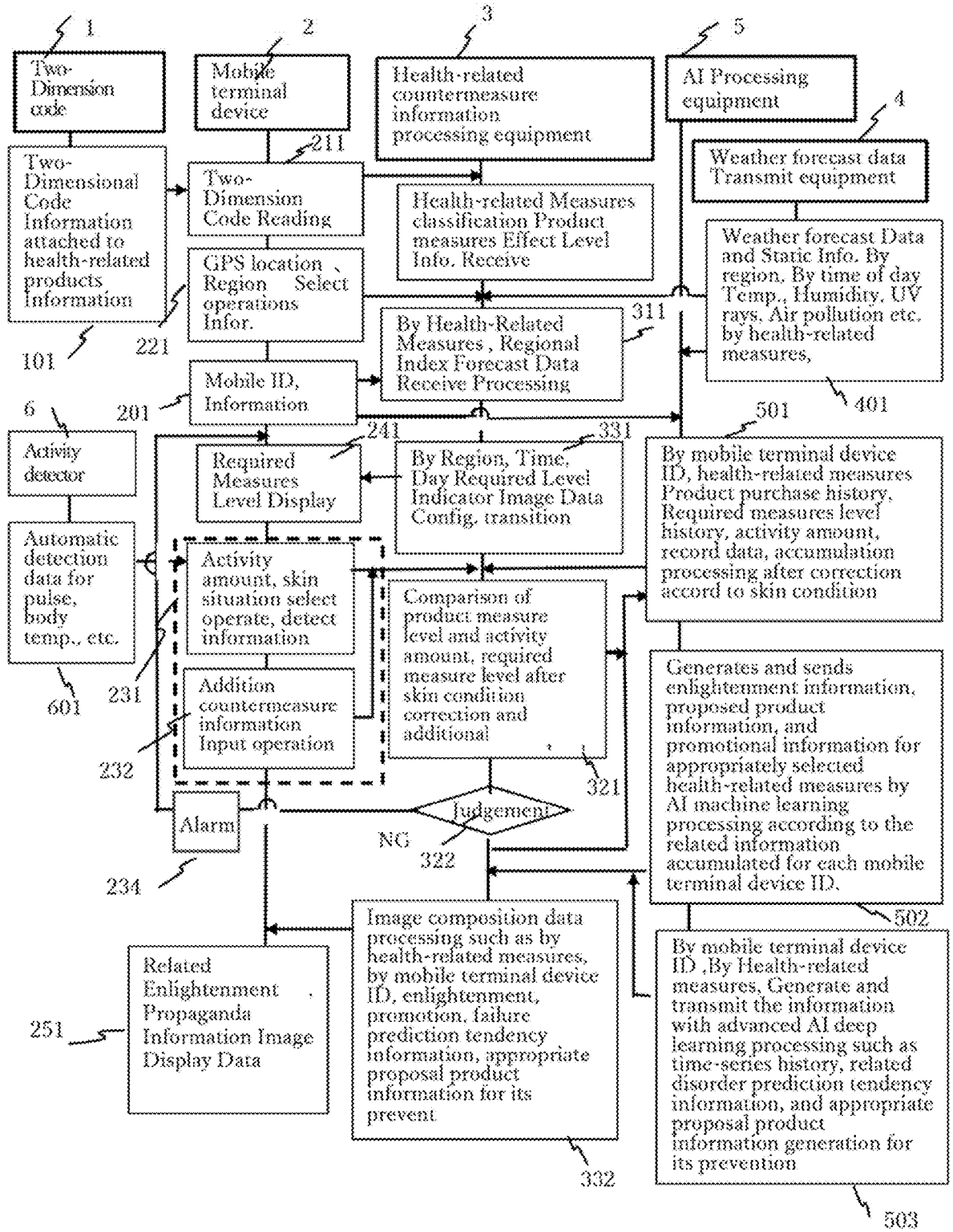
FIG. 14 is a flowchart which shows the operation of this embodiment.

FIG. 14 is a flowchart showing the operation of this embodiment.

First, an embodiment of the first embodiment of the present invention will be described.

As a health-related measure classification, a cap-type hat 11 having a cooling function for cooling the back of the head with the heat of vaporization of water, for example, the above-mentioned health measure classification called "heat stroke countermeasure" and its countermeasure effect level information, Manufacturer, product part number information, etc.

Recorded Specific Information 101 of the Product

A two-dimensional code 1 such as a QR code is attached.

The two-dimensional code information 101 can be obtained by the two-dimensional code reading unit (obtaining unit) 21 through the image pickup element 120 provided on the back side or the front side of the mobile terminal device 2.

Further, since the built-in GPS receiver 22 obtains the current position information of the mobile terminal device 2, the current area information of the user or the operation information 221 by the area selection means 123 selected by the user is obtained.

In addition, the health-related countermeasures processing equipment 3 can obtain information 201 that identifies the user, such as the telephone number or registration ID of the mobile terminal device 2.

This information is transmitted to health-related countermeasures processing equipment 3 in a remote place through the internet communication network.

The health-related countermeasures processing equipment 3 is also operated by the Meteorological Agency, etc.

via the Internet communication network from the weather forecast transmission equipment 4, such as temperature, humidity, ultraviolet ray amount, pollen and PM2.5 of air pollution scattering amount, etc. Obtain data transmission of weather forecast information such as air pollution amount and transmission of past related statistical data 401 in FIG. 14.

Next, the health-related countermeasures processing equipment 3 is based on the information obtained from the weather forecast transmission equipment 4, for example, when the health-related measure classification is heat stroke countermeasure, the heat index WBGT shown in FIG. 5(*a*). On the value table graph 125, a partition line 53 for dividing the area into the required countermeasure level 126 for caution, strict caution, etc. is generated, and further, the area division information from the mobile terminal device 2 is obtained, and the area division information is obtained on the graph 125. The operation of generating and transmitting the information of the range 54 of the predicted heat index value for each region, the region, the time, the required countermeasure level index image data composition, and the transmission 311 are performed.

As a result, the mobile terminal device 2 displays the health-related countermeasure classification display 121, the caution of the required countermeasure level, the character word display 122 such as caution, the predicted time, the day selection display 124, and the countermeasure index graph display (shown in FIG. 1). In the case of heat stroke countermeasures, the heat index graph 125, the numerical display 126 of the required countermeasure level, and the two-dimensional code attached to the product are incorporated. Countermeasure effect generates screen configuration data such as level 127 and transmits it to the mobile terminal device 2 as a transmitting unit. The mobile terminal device 2 performs an operation 241 to display a screen as shown in 121 to 127 of FIG. 1 incorporating these.

Since the present invention is configured in this way, the specifications of the product, such as countermeasures against heat stroke, can be obtained by simply reading the two-dimensional code 1 attached to the product by the user of the mobile terminal device 2. Obtains a health-related measure classification category classified based on function and performance, and a display 127 of the current measure effect level of the product in the classification category.

Furthermore, the index prediction value range of health-related countermeasures such as the future heat index such as today, tomorrow, and the day after tomorrow, which is generated from the weather forecast information data of the area where the user is currently located or the area selected by the user. From the comparison between 54 and the division range 53 of the prediction required countermeasure level of the relevant division, it is possible to know the required countermeasure level 122 by displaying characters such as warning and strict warning at the selected predicted date and time 124.

Therefore, it is possible to compare the display 127 of the countermeasure effect level numerical value of the product with the display 126 of the numerical value of the required countermeasure level for each region and each predicted date and time, and to make a comparison judgment as to whether or not it is appropriate. It can be used as an information system for auxiliary means for related countermeasures.

Figure 4:
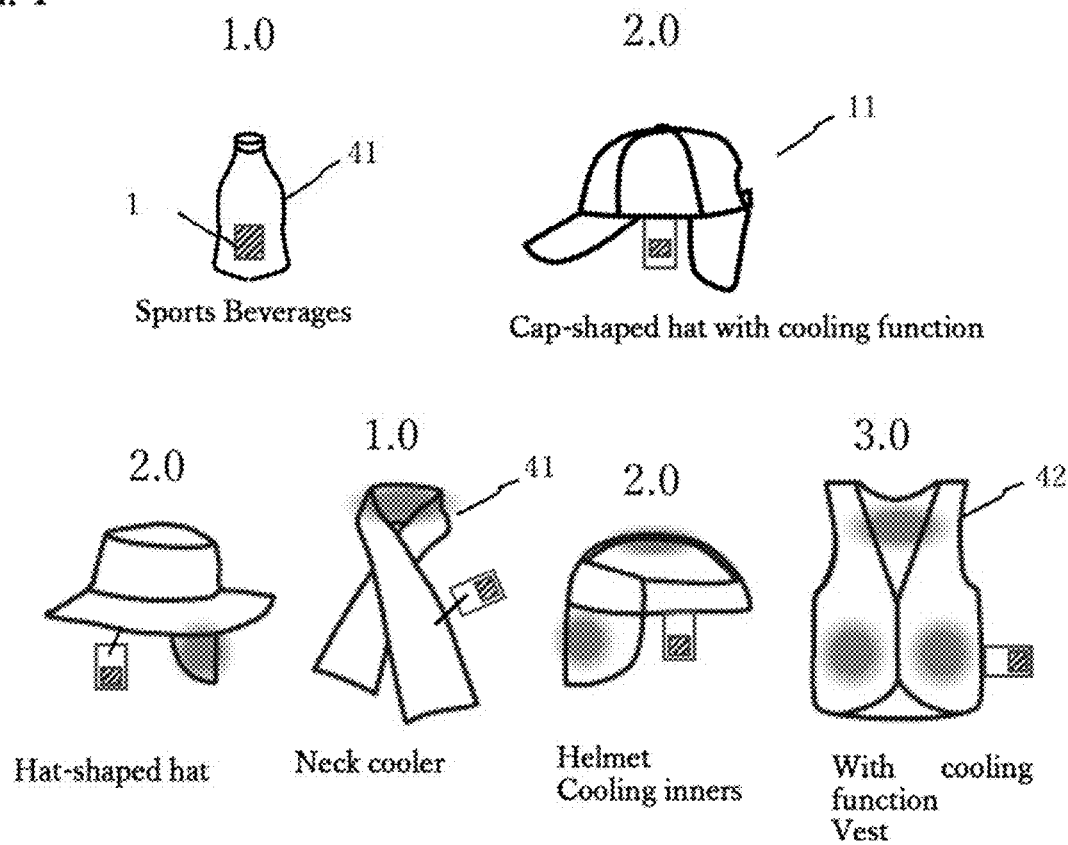
FIG. 4 is a diagram showing an example in which a tag printed with a two-dimensional code having the corresponding countermeasure effect level information is attached to a "heat stroke countermeasure" product as a health-related countermeasure category (classification) in the present embodiment. The numerical values shown at the top of the schematic diagram of each product are examples of numerical values indicating the countermeasure effect level of "heat stroke countermeasures" of the product.

For example, in the case of heat stroke countermeasures, if the specifications of a cap-type hat with a cooling function and a product with a countermeasure effect level 2 are planned, and if it is judged to be inappropriate from the above comparison, a product with a higher countermeasure effect level, for example, It can be determined whether the best 42 with a cooling function of the countermeasure effect level 3 is used, or the neck cooler 41 of the same countermeasure effect level 1 of FIG. 4 is additionally used.

These can be displayed instantly on a mobile terminal device, and for example, the user has a great effect of being able to instantly determine what kind of heat stroke countermeasure product should be selected for the schedule of going out the day after tomorrow.

Next, one embodiment of the second embodiment of the present invention will be described.

Display the correction of the required countermeasure level for each health countermeasure classification according to the amount of activity and physical condition of the user.

Figure 5A:
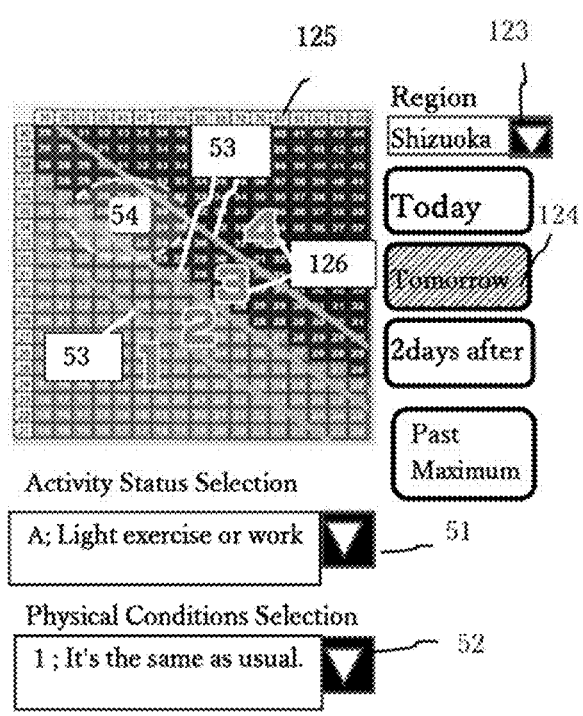
FIG. 5A is a measure against heat stroke displayed on the mobile terminal device in this embodiment. The predicted value of the heat index of the designated area is shown on the heat index table, and the required countermeasure level is shown. This is an example of the plan view shown.
Figure 5B:
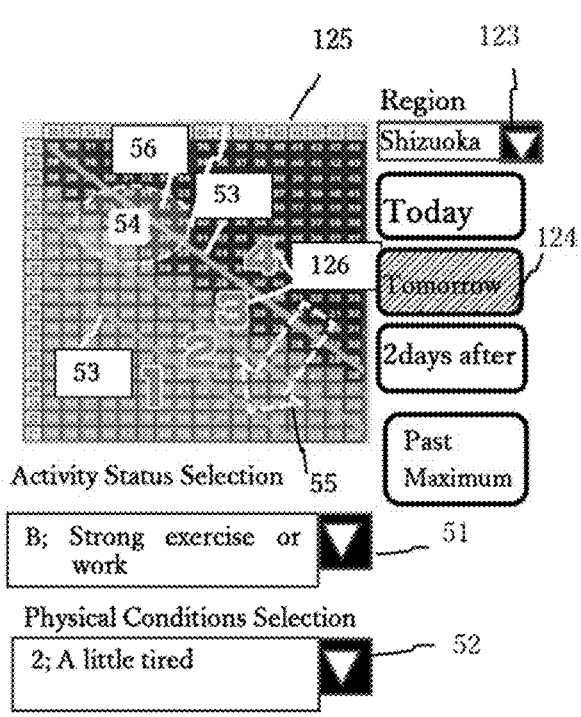
FIG. 5B selects activity status and physical condition (physical condition, etc.) It is a diagram showing how the graph partition value of the required countermeasure level has moved downward after selection.

As an example of this embodiment, the required countermeasure level data for heat stroke in FIG. 3B and the heat index as heat stroke countermeasure displayed on the mobile terminal device in this embodiment of FIGS. 5A and 5B. It will be explained that Table 125 shows the predicted value 54 of the heat index of the designated area and also shows the required countermeasure level 126.

For example, the required countermeasure levels such as heat stroke caution and strict caution are classified according to the range according to the published heat index value table 125.

At this time, if the amount of activity and the physical condition of the user (target person) can be taken into consideration and corrected, it is considered that a more appropriate required countermeasure level can be obtained.

Therefore, as shown in (b) of FIG. 3, an example of the correction value data is "A: light exercise or work", "B: strong exercise or work".

And "C: Maximum competing exercise or heavy work" like at an international sporting event or severe work by the means 51 for selecting the amount of activity is provided.

Next, an input means 52 for correcting the physical condition (physical condition, etc.) of the user is also provided.

As a result, from health-related indicators such as the heat index value, data for correcting the partition value 53 of the required measure level classification, activity amount, required measure level data for heat stroke after correction according to the physical condition, FIG. 3(*b*) is configured.

The partition line 53 for the required countermeasure level division in the heat index WBGT value table graph 125 is shown in FIG. 5A.

For example, select "A; light exercise or work" as an activity status selection, and select a physical condition as "1; same as usual", and is displayed as the partition value line 53 of the required countermeasure level at the correction value in that case.

For example, here, as shown in FIG. 5B, the means 51 for selecting the amount of activity selects "B; strong exercise or work" scheduled at the predicted date and time, for example, "tomorrow" 124. When "2; a little tired" is selected by the physical condition selection means, the partition line 53 is shown moving a little down.

Applicable required countermeasures after correction of the range 54 of the predicted heat index of the area where the heat index value as the level data is corrected so that the whole value shows the lower value is in the downward direction of the partition line 53. Due to the movement of, the range of the required countermeasure level 4 of the level of "Danger, exercise and work is canceled"

The position is corrected so that it is included a lot of level 4 area.

This is shown as a range 56. In the arrow imaginary line 55, the partition lines 53 of the required countermeasure levels 1 to 4 are moved by the operation of the activity status selection 51 and the physical condition status selection 52.

The comparison between the required countermeasure level after this correction and the countermeasure effect level of the currently used product, and the comparison by adding the countermeasure effect level of the additional countermeasure product are shown in the operation flow of FIG. 14, "Compare of product measure level and activity amount, required measure level after skin condition correction and additional countermeasure level" 321 and "Judgment" 322.

It is processed by the Health-related Measures Effect Level processing Section 32 in the block diagram of FIG. 2.

If this judgment is NG (failure), it is possible to return to the required countermeasure level prediction display 241 and select the amount of activity, you can add additional countermeasures by the additional countermeasure information input operation 232, and obtain the judgment 322 again.

Here, the selection of the amount of activity is not about three steps in the example shown in FIG. 3B.

Further, according to the present invention, the classification of the physical condition can be performed in multiple stages, such as not only the above-mentioned degree of physical fatigue but also the physical condition such as body temperature and sweating.

In addition, the scheduled exercise can be selected in more detail in multiple stages, taking into consideration the surrounding environment such as ventilation of the work site and the presence or absence of shade.

If the physical condition and the planned amount of activity can be selected and operated in detail in this way, the partition value of the required countermeasure level 53 is set more detail. However, it can be configured so that it can be corrected in multiple stages in more detail.

Furthermore, if the amount of activity and the physical condition such as the physical condition can be selected and operated in detail separately, the partition value of the required countermeasure level 53 can be corrected in more fine steps in multiple stages. It can also be configured.

Further, as shown in FIG. 2, if the activity amount detector 6 for the pulse and body temperature of the human body, which is incorporated in the mobile terminal device 2 or communicates by short-distance radio or the like, is connected the activity amount such as the pulse rate.

The automatic detection data information 601 can be taken in as the detection information 231 of the mobile terminal device.

Since the amount of activity can be automatically and constantly measured, it is possible to automatically and constantly correct the content of the required countermeasure level.

Further, it is possible to realize the mobile terminal device 2 of the system of the present invention, which is an integrated type, for example, in the shape of a wristwatch, in which the activity amount detector 6 is incorporated so as to come into contact with the contact surface of the skin such as a human arm.

For example, if the mobile terminal device 2 is worn by a long-time athlete such as a marathon or a triathlon competition, the change in the activity amount of the athlete can be detected every moment. In addition, the correction of the necessary countermeasure level can be obtained in detail.

If the prediction of the weather information including the position information on the day of the competition deviates significantly from the content of the countermeasure effect level prepared in advance, it can be determined in Flow 322 that it is not appropriate.

At that time, a system capable of issuing an alarm 232 from the alarm device 29 can be constructed.

It is possible to prevent athletes such as competitions from suffering from heat stroke.

The same can be said for workers who perform heavy labor for a long time outdoors in high temperature weather.

In addition, the two-dimensional code information 1 attached to the product is not merely a rating numerical value as shown in FIG. 4 as the countermeasure effect level.

For example, in the case of the sports drink 41 shown in FIG. 4, which part of the body is cooled and protected as a measure against heat stroke, for example, with respect to the amount of ingredients expected to be effective as a measure against heat stroke and the required countermeasure level. It is possible to enter more detailed 2D code information 1 of how much intake is a guide.

The mobile terminal device 2 of the system of the present invention can read this detailed two-dimensional code information.

Therefore, the mobile terminal device 2 can calculate the required countermeasure level from, for example, the heat index WBGT value range of the area predicted from the weather prediction data of the day after tomorrow.

Furthermore, for example, the amount of activity and physical condition of oneself at a sporting event scheduled for the day after tomorrow (physical condition such as physical fatigue and illness, and physical characteristics such as skin condition). Is configured so that it can be selected in detail.

As a result, detailed multi-step correction of required countermeasure level information, for example, "whether you are diligently taking water or salt", "whether your face is hot", "whether your muscles are jerks", "headache" Through the mobile terminal device 2, detailed cautions and preventive confirmation information for countermeasures against heat stroke, such as "Are you feeling nausea?", Can be notified to the user.

Further, it is assumed that the two-dimensional code 1 incorporates information such as which part of the body is a product to be cooled and protected as a measure against heat stroke.

Then, the information can be received by the mobile terminal device 2, the Internet network, the health-related countermeasures processing equipment 3, or the AI processing equipment 5. Therefore, from the specification information of the other product stored in the memory, the promotion information of the product capable of cooling and protecting the other part of the body part can be displayed on the enlightenment promotion information display part 151.

Next, one embodiment of the third embodiment of the present invention will be described.

An AI processing equipment 5 connected to an internet line is provided in a part of the system of the present invention.

The AI processing equipment (receiving unit) 5 receives weather forecast data such as temperature, humidity, and ultraviolet amount for each health-related measure, region, and predicted date and time, and statistical information data 401 from the weather forecast transmission equipment 4.

The mobile terminal device 2 can also be a so-called smart phone that can display various information via an Internet communication network and also has a telephone function.

In this case, the mobile terminal device 2 has unique telephone number information or information for identifying the individual user by the mobile terminal ID information 201 registered by the user, and is via the health-related countermeasures processing equipment 3. Alternatively, it can be transmitted directly to the AI processing equipment 5.

Further, from the health-related countermeasures processing equipment 3, it is possible to receive the comparison information 321 and the judgment information 322 of the product measure effect level, the required measure level after the activity amount correction, and the additional measure level.

From these, the AI processing equipment 5 can accumulate processing 501 of mobile terminal operation history information such as mobile terminal ID number, health-related measure product purchase history, required measure level history, and activity amount selection information, and at the time of the operation history. Based on the weather forecast data for each health-related countermeasure classification in the region, data accumulation processing is performed for the health-related forecast index and its required countermeasure level.

In the AI processing equipment 5, the enlightenment information of appropriately selected health-related countermeasures by machine learning processing, the proposed product information, etc. from the reading information of the two-dimensional coat accumulated for each mobile terminal ID number in each health-related classification category, Generates transmission information of advertising information.

Then, the information 502 is then transmitted to the mobile terminal 2 via the health-related countermeasures processing equipment 3.

In addition, the activity amount selection operation and the correction required measure level after the additional measure information input operation, and the activity amount automatic detection data information such as pulse and body temperature change automatically acquired by the activity amount detector and the health-related record high by region. Index values etc. are added.

They are classified by health-related countermeasures classification or compound classification, and are highly advanced such as generation of health-related countermeasure history, related disorder prediction tendency information, and appropriate proposal product information for prevention by individual by mobile terminal ID number. Information generation 503 by the learning process is performed.

Then, the information can be transmitted to the mobile terminal device 2 via the health-related countermeasures processing equipment 3.

As a result, the mobile terminal device 2 can display related enlightenment and publicity information as shown in FIG. 15D and notify the user.

For example, as an example of the machine learning process generation information 502 of the AI processing equipment 5, an example of the display of the image display data 251 displayed on the mobile terminal device 2 is shown.

As an example of the display in 151 of FIG. 15C, for example, "Tomorrow's heat stroke prediction countermeasure level is "strict caution". Please prepare the XX product of the countermeasure effective level 3 of the previous purchase. Please take water diligently. "521 or "The product XX you have now is not enough for the heat stroke countermeasure prediction level the day after tomorrow. We recommend that you prepare for the addition of a new product XXX that cools your neck." 522 can be displayed to inform the user.

Furthermore, as an example of the deep learning process generation information 503 of the AI processing equipment 5, "From your past product usage history data, heat stroke is "dangerous" according to the predicted activity amount scheduled for tomorrow entered.

We recommend that you review the amount of activity 531 or something "Based on your activity amount, pulse, body temperature measurement history data and the heat stroke prediction required countermeasure level in the XX area the day after tomorrow, the countermeasure product is XX, and the predicted heat stroke symptom of moderate degree II "headache" "To prevent "feeling uncomfortable", we recommend taking Xml/h or more of product XX containing XX ingredients!"532 etc. are displayed and the user is notified.

To explain these collectively, the required countermeasure level information, the amount of activity, and the physical condition information are classified according to the mobile terminal device 2 specified by the mobile phone number or the ID number entered by the user, and according to the health measure classification. A means 501 for accumulating the required countermeasure information after the correction is provided.

In addition, a means for comparing and organizing these in chronological order will be provided.

As a result, the mobile terminal device can generate failure occurrence prediction information for each related classification category, recommended enlightenment information for countermeasures, and related product promotion generation information 503 generated by the AI processing equipment 5 for each classification category via the Internet communication line.

In this way, the user of the system of the present invention can use the past data of weather prediction, the prediction data of the near future, the input past history of the activity amount of the individual user, and the pulse rate and body temperature obtained from the activity amount detection unit 6. It can be obtained from the historical data of the history.

These can be guessed and deep learning process, for example, the day after tomorrow It is possible to obtain powerful health-related countermeasure assistance means to obtain related enlightenment knowledge information generation, product selection, suitability, additional preparation, etc. You can get proposal promotion information for each applicable health-related countermeasure category at the time of the near future.

Up to this point, the first, second, and third embodiments of the present invention have been described mainly for heat stroke countermeasures as health-related countermeasure classification categories.

Therefore, as other health-related countermeasure classification categories, harmful ultraviolet rays countermeasure and the classification of pollens countermeasures should be explained. However, since it includes many components and operation flows similar to those described above, the contents described mainly in the heat stroke countermeasure classification will be omitted in the same manner.

Therefore, next, an embodiment of the present invention regarding the harmful ultraviolet ray countermeasure classification as a health measure classification category will be described. An index called the UV index has been published as an index for measures against harmful ultraviolet rays.

FIG. 6A is an example of UV prediction data for the near future, for example, today, tomorrow, and the day after tomorrow, by region.

The UV index is transmitted from a Weather forecast Data Translating equipment such as a weather forecasting organization to the Internet communication network.

FIG. 6B is an example for the harmful ultraviolet rays countermeasure classification of the system of the present invention.

As the physical condition set as, for example, it is an example of required countermeasure level data for harmful ultraviolet rays countermeasures based on the corrected UV index in consideration of the skin condition.

Figure 7:
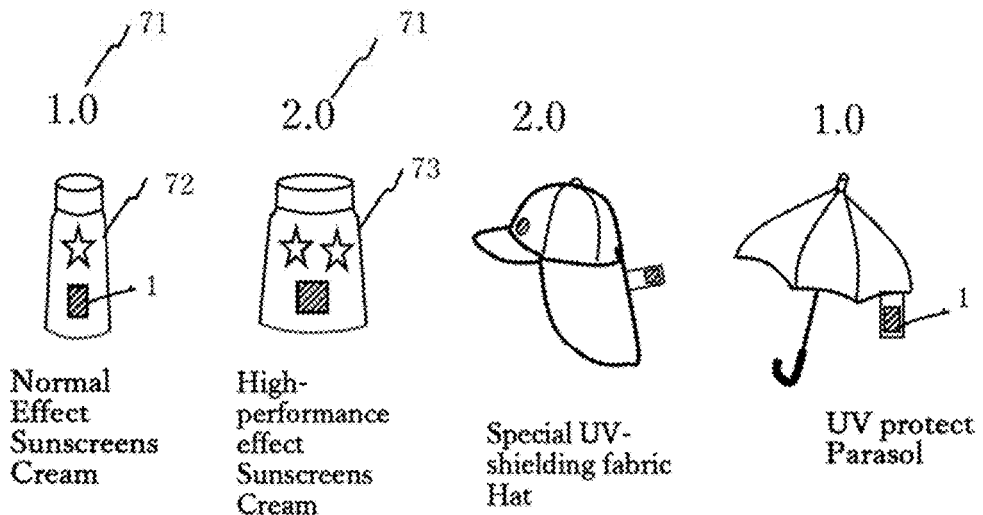
FIG. 7 is a diagram showing an example in which a tag printed with a two-dimensional code having information on the effect level of countermeasures against harmful ultraviolet rays is attached as a health-related countermeasure category. The numerical values shown at the top of the schematic diagram of each product are examples of numerical values indicating the countermeasure effect level for "harmful ultraviolet rays countermeasures" of the product.

FIG. 7 is a diagram showing an example in which a tag printed with a two-dimensional code 1 having countermeasure effect level information is attached to the corresponding product in the harmful ultraviolet ray countermeasure classification.

The numerical value shown at the upper part of the schematic diagram of each product is an example of the numerical value showing the countermeasure effect level 71 for the "harmful ultraviolet rays countermeasure" of the product.

In the figure, 72 represents a sunscreen cream having a normal effect, and the countermeasure effect level is 1, while 73 high-performance sunscreen creams have a countermeasure effect level of 2.

Figure 8A:
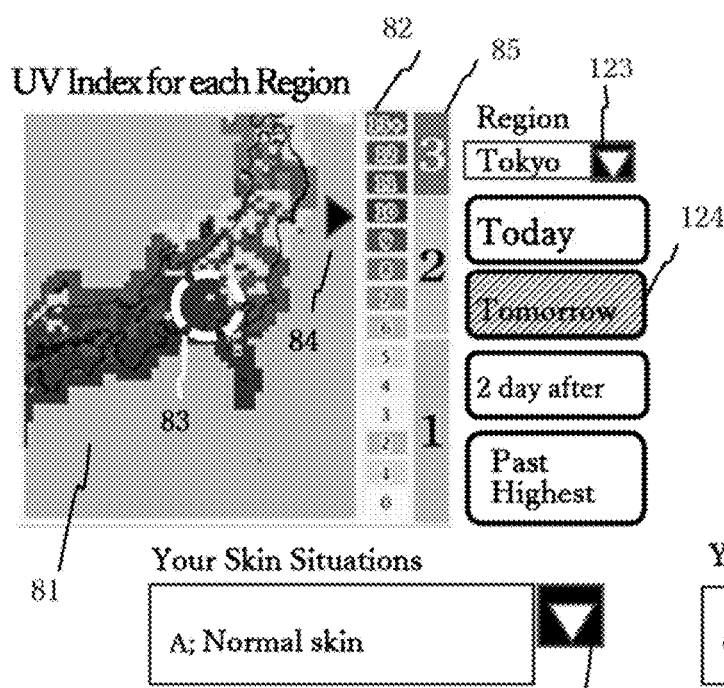
FIG. 8A shows the UV index for each region as a countermeasure against harmful ultraviolet rays displayed on the mobile terminal in the present embodiment, and shows the predicted value of the UV index for the designated region. Moreover, it is an example of the figure which shows the UV necessary measure level value. Similarly.

In FIG. 8A, the figure display 81 shows the predicted value of the UV index for each region of "tomorrow" 124 of the means for selecting the predicted date and time, for example, as a measure against harmful ultraviolet rays displayed on the mobile terminal device 2. There is a UV index level display graph 82 that can be seen at a glance by comparing the values. 83 is a geographical area range selected by the area selection means 123 or detected by GPS (GPS signal), and the UV index value is configured and displayed so that the arrow 84 indicates the value.

Reference numeral 85 denotes a sorting graph display of the necessary countermeasure level. In the illustrated example of FIG. 8A, the region is selected by the region selection means 123, for example, the predicted UV index value of "Tomorrow" 87 in the illustrated range 83 of Shizuoka Prefecture is the value 10 indicated by the arrow 84.

From the vertical relative positional relationship of the required countermeasure level graph 85 when the user's skin condition selection means 88 is "A; normal skin", it is shown that the required countermeasure level is a value of 2.

Figure 8B:
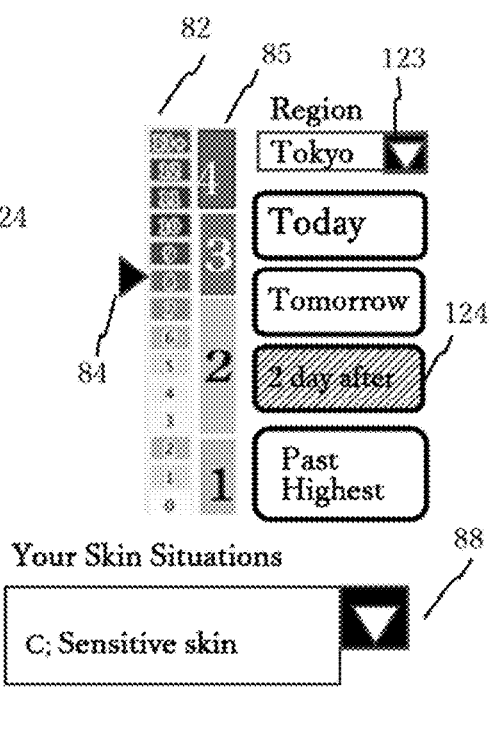
FIG. 8B is the correlation between the UV index and the necessary countermeasure level when "sun allergic skin" is correct selected in the user's skin condition selection. It is a figure which shows to correct.

If, as in the example shown in FIG. 8B, the skin condition of the physical condition information selected by the user's skin condition selection means 88 selects "C; Sunlight allergy" do.

Even though the predicted UV index of "the day after tomorrow" 124 is a value of 8 and a value of −2 lower than the value of "tomorrow", the relative positional relationship is corrected and the movement changes, and the necessary countermeasure level 85 is a stricter value. It indicates that the position of 3 is indicated and displayed.

As described above, when the health measure category is the measure against harmful ultraviolet rays, the user has, for example, a means 88 for selecting the physical condition of the user, for example, "skin condition".

As a result, the indicated position of the harmful ultraviolet ray necessary countermeasure level graph 85, which is partitioned relative to, for example, the UV index value of the harmful ultraviolet ray index for each predicted date and time such as tomorrow and the day after tomorrow, can be corrected and displayed. Therefore, the necessary countermeasure level value corrected by the skin condition selection can be obtained, and the system is effective in notifying the user of appropriate harmful ultraviolet rays countermeasures in consideration of individual differences in the skin condition.

For example, if the user's skin condition selection 88 selects "C; Sunlight allergy", the UV index value in the Shizuoka prefecture range of "the day after tomorrow" is 8, and the required countermeasure level after correction is level 3. It becomes.

Therefore, if a sunscreen cream having a high performance effect of UV protection effect level 2 is used and a parasol having a UV protection effect level 1 is added and used, the UV protection effect level 3 can be added and secured.

Therefore, it is possible to construct a system that instantly shows that the appropriateness judgment is "OK", which has a great effect.

Next, an embodiment of air pollution pollen/PM2.5 countermeasures will be described with the embodiment of the present invention as a health-related countermeasure classification category.

The forecast data for the amount of pollen or PM2.5 scattered by region is also transmitted from the weather forecast transmission equipment 4 of the weather forecasting agency to the Internet line communication network.

The health-related countermeasures processing equipment 3 receives the various weather forecast data receive processing section unit 31 in the same manner as described above.

For example, as shown in FIG. 9A, pollen/PM2.5 scattering predicted values are arranged and stored in memory according to the predicted date and time such as region, tomorrow, and the day after tomorrow, or others.

In addition, FIG. 9B shows the table data of pollen or PM2.5 scattering amount values according to the required countermeasure level such as "A; normal", "B; a little sensitive", "C; very sensitive"

It is corrected by selecting the degree of hypersensitivity to pollen or PM2.5 of the user.

The unit of the numerical value in the figure is expressed by the quantity (pieces) of pollen and PM2.5 per cubic centimeter.

The health-related countermeasures processing equipment 3 receives various weather prediction data and is processed by the processing section unit 31 and is processed as shown in 311 of the operation flow of FIG. 14.

Figure 10:
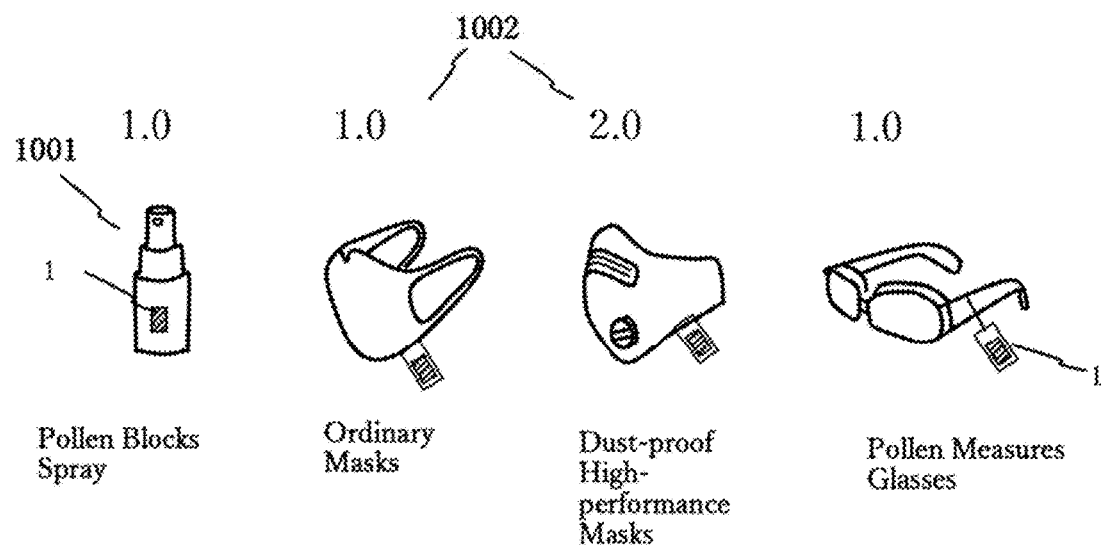
FIG. 10 is a figure which shows the example which attached the tag which printed the 2D code which has the corresponding countermeasure effect level information to the "pollen measures" product as a health-related countermeasure classification in this embodiment. The numerical values shown at the top of the schematic diagram of each product are examples of numerical values indicating the level of countermeasure effect on "pollen countermeasures" of the product.

On the other hand, FIG. 10 is a diagram showing an example in which a two-dimensional code such as a QR code having countermeasure effect level information is attached to a corresponding product in the pollinosis countermeasure category as a health-related countermeasure category.

The two-dimensional code 1 in which information on the pollen countermeasure effect level 1002 is incorporated into the pollen block spray 101 and various masks is attached to each product.

Figure 11A:
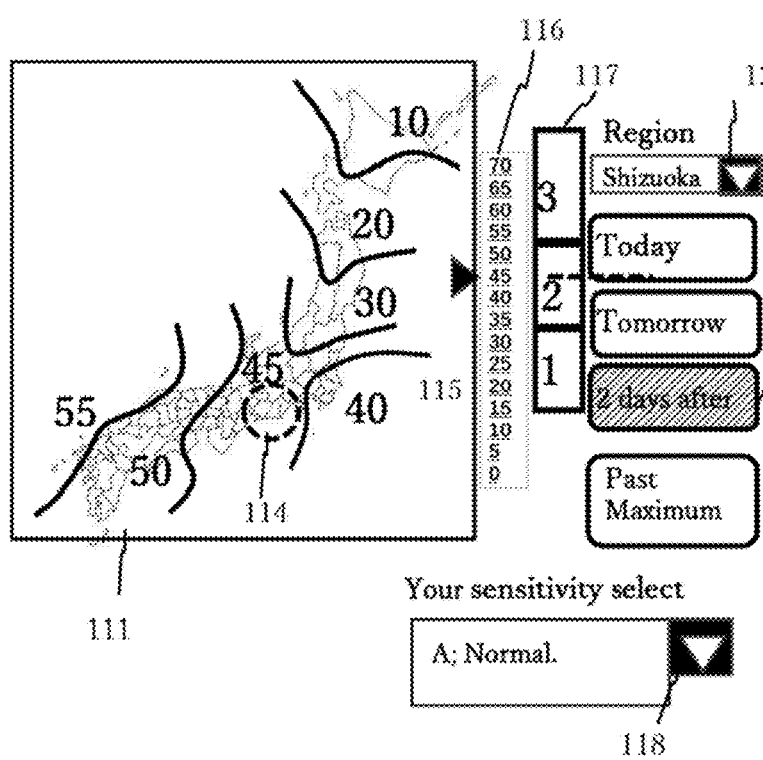
FIG. 11A is an example of a diagram showing a predicted value of pollen scattering amount for each region and showing a necessary countermeasure level as a countermeasure against pollinosis.
Figure 11B:
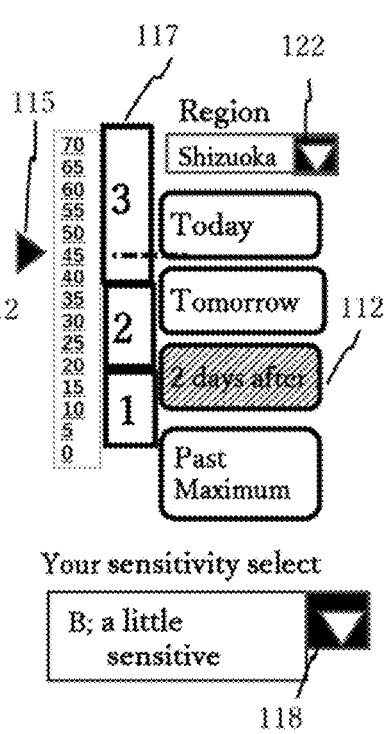
In FIG. 11B, "B; Slightly sensitive" is selected as the degree of hypersensitivity situation selection. In that case, it is a figure explaining that the correlation between the amount of pollen scattering and the necessary measure level is corrected.

FIGS. 11A and 11B are diagrams illustrating the display contents on the display unit of the mobile terminal device 2 constituting the system of the present invention in the pollinosis countermeasure category.

FIG. 11A shows, for example, the predicted value of pollen scattering amount for each region of "the day after tomorrow" 112 as a measure against pollen displayed on the mobile terminal device 2.

In the example of FIG. 11A, the selected area range 114 is displayed.

Guideline 115 indicates and displays the predicted pollen dispersal amount in the area range 114 on the pollen dispersal amount scale 116

For example, in the case of FIG. 11A, the area is Shizuoka Prefecture, and the predicted value of the amount of pollen or PM2.5 scattered the day after tomorrow is 45 (45 pollen per cubic square centimeter).

In the pollen or PM2.5 countermeasure level meter 116, the required countermeasure level 117 indicates level 2.

Here, in FIG. 11B, as a means for selecting the physical condition, the user-sensitive degree situation selection means 118 is prepared.

You can change the selection of the degree of hypersensitivity to your pollens or PM2.5 value from "A: normal" in FIG. 11A to "B; a little sensitive". In this case, the pollen or PM2.5 countermeasure level meter 117 is corrected to the relative position indicating relationship with the pollen or PM2.5 scattering amount set in "correction of sensitivity and required countermeasure level" in FIG. 9B.

Therefore, the required countermeasure level will be raised from 2 to 3.

In this way, for example, pollen countermeasures are taken from the health-related countermeasure classification categories incorporated in the two-dimensional code 1 such as the QR code attached to the product, and the countermeasure effect level is read.

On the other hand, through the Internet communication network, future forecast data of the amount of pollen or PM2.5 scattered by region, such as tomorrow and the day after tomorrow, will be obtained from the meteorological forecasting organization.

In addition, it has a means for inputting the expected activity amount or physical condition of the user (user) at that time.

Therefore, the product can provide a system in which the suitability of the pollen or PM2.5 countermeasure level is displayed on the mobile terminal device 2 at hand, for example, with respect to the action schedule of the user the day after tomorrow.

Therefore, the user can expect a great effect that the advance preparation for pollen and PM2.5 countermeasures can be promptly and adapted based on the future weather forecast of the day after tomorrow.

In addition, the system of the present invention can further take measures against pollution based on the regional distribution prediction data of fine particulate particles of air pollution, yellow sand and other pollutants.

In addition, measures against winter cold, mainly based on regional cold temperature forecasts, migraine measures based on changes in temperature, humidity, and atmospheric pressure, and health-related measures such as low back pain.

Although various classification categories such as countermeasure classification can be considered, the system of the present invention can be obtained by configuring them in almost the same manner.

Further, in the description of the embodiment of the present invention, it is explained that the two-dimensional code information 1 is attached to the product according to the health-related measures classification category.

It can also be printed and attached to a cloth tag that indicates quality indication, etc., or a paper specification indication tag that is worn when the product is purchased but is generally separated when used.

In addition, the product is identified by the image of the product and displayed in the vicinity of the product, so-called WEB display for identifying promotion and display in the catalog.

Add that it includes to do of this invention.

Figure 15A:
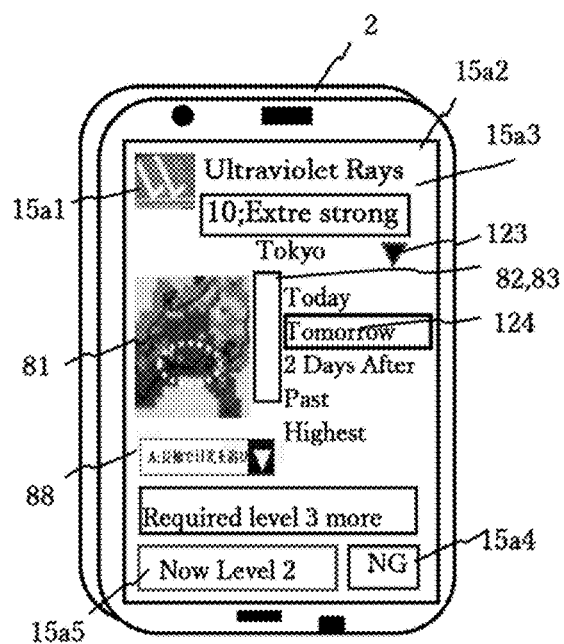
Figure 15B:
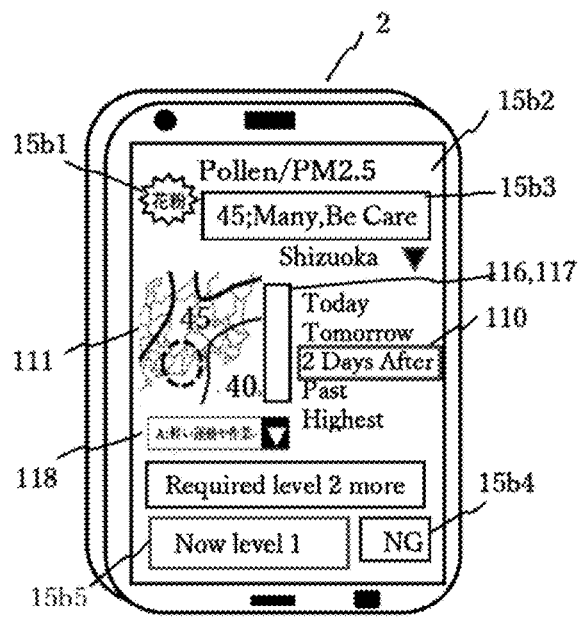

Further, here, instead of the two-dimensional code 1, among the various information displays on the WEB displayed by the mobile terminal device 2, the marks for each health measure classification category, such as 15$a$1, 15$b$1, 15$c$1, etc., in FIGS. 15A, 15B, 15C are displayed. Alternatively, a combination of the mark or the like and the two-dimensional code can also be used.

Alternatively, the mark is image-recognized to obtain the health-related measure classification, and the character information corresponding to the health measure classification and the information obtained by linking from the product photo image are incorporated into the two-dimensional code 1. The information system of the present invention can be constructed by substituting the same information as the above.

Further, the mobile terminal device 2 is mainly assumed to be a mobile phone or a smart phone having a built-in image sensor 120 for reading a two-dimensional code such as a QR code.

However, a similar information system can be constructed even with a fixed-place type personal computer unit in which the above-mentioned two-dimensional code reader can be separately connected and communicated.

INDUSTRIAL APPLICABILITY

The present invention relates to various health-related countermeasure products such as heat stroke countermeasures, harmful ultraviolet rays countermeasures, pollen/PM2.5 countermeasures, etc.

It enables appropriate product selection in consideration of the amount of activity and physical condition of the person.

Therefore, it is an information system that is useful for promoting the use and sales of these products and has a very high possibility of being used industrially.

DESCRIPTION OF THE REFERENCE NUMERALS

1 Two-dimensional code such as QR code
2 Mobile terminal device
3 Health-related countermeasures information processing equipment
4 Weather forecast transmit equipment
5 AI processing equipment
6 Activity detector
15$a$1 Display mark for harmful ultraviolet rays
15$b$1 Display mark pollen or PM2.5 countermeasure
15$c$1 Display mark for heat stroke countermeasure
15$a$2 Screen display example of mobile terminal device in case of harmful ultraviolet rays countermeasure
15$b$2 Screen display example of mobile terminal device for pollen or PM2.5 countermeasures
15$a$3 Required countermeasure level character display example for harmful ultraviolet rays countermeasures
15$b$3 Required countermeasure level character display example for pollen or PM2.5 countermeasures
15$a$4 Judgment display of Harmful UV protection
15$b$4 Judgment display of pollen or PM2.5 countermeasure

15a5 Current status of harmful UV protection effective level

15b5 Current status of pollen countermeasures effective level

The invention claimed is:

1. A health-related countermeasure information system, comprising:
  a mobile terminal device; and
  a health-related countermeasure information processing device, wherein
  the mobile terminal device includes:
    a two-dimensional code reader configured to read a two-dimensional code attached to a health-related countermeasure product or read the two-dimensional code displayed in a vicinity of an information for identifying the health-related countermeasure product, the two-dimensional code including the health-related countermeasure classification information; the health-related countermeasure classification information including at least one of heat stroke countermeasure, harmful ultraviolet rays countermeasure, pollen countermeasure and PM2.5 air pollution countermeasure and
    a GPS receiver configured to obtain a current position information of the mobile terminal device from a GPS signal or an input unit for selecting an area by a user,
  the health-related countermeasure information processing device is configured to:
    receive a weather forecast information through an internet communication network for each health-related countermeasure classification included in the two-dimensional code read by the two-dimensional code reader, each area location included in the current position information obtained by the GPS receiver or included in the area selected by the user via the input unit and each date, the weather forecast information including a temperature value and a humidity value as the heat stroke countermeasure, an ultraviolet rays amount as the harmful ultraviolet rays countermeasure, a pollen amount as the pollen countermeasure, and PM2.5 amount as the PM2.5 air pollution countermeasure; and
    generate a required countermeasure level prediction information from the weather forecast information required for each of the health-related countermeasure classification and transmitting the required countermeasure level prediction information to the mobile terminal device, and
    the required countermeasure level prediction information is configured to be displayed on the mobile terminal device for each of the health-related countermeasure classification, each of the area location and each of the date.

2. The health-related countermeasure information system, according to claim 1, wherein
  an information including a health-related countermeasure effect level specific to each of the health-related countermeasure product is included in the health-related countermeasure classification information, and
  the health-related measure information processing device is configured to determine an appropriateness of the health-related countermeasure effect level by comparing the health-related countermeasure effect level with the required countermeasure level prediction information and display a result of the appropriateness on the mobile terminal device.

3. The health-related countermeasure information system, according to claim 1, wherein
  the health-related measure information processing device is configured to adjust and correct a division value of the required countermeasure level prediction information of each of the health-related countermeasure classification by a predetermined value according to an activity amount and a physical condition inputted from the mobile terminal device by the user, and
  the mobile terminal device is configured to display the corrected required countermeasure level prediction information of each of the health-related countermeasure classification.

4. The health-related countermeasure information system, according to claim 1, wherein
  an input history of an activity amount and a physical condition and a display history of the required countermeasure level prediction information of each of the health-related countermeasure classification are accumulated for each of the mobile terminal device identified by a mobile phone number or an ID number entered by the user,
  a countermeasure enlightenment information or a countermeasure product promotion information for each of the health-related countermeasure classification preliminarily selected in association with the input history or the display history is configured to be displayed on the mobile terminal device.

* * * * *